United States Patent [19]

Yasnitsky et al.

[11] 4,364,393

[45] Dec. 21, 1982

[54] ABSORBABLE SURGICAL SUTURE MATERIAL BASED ON MONOCARBOXYCELLULOSE AND METHOD FOR PRODUCING THE SAME

[76] Inventors: Boris G. Yasnitsky, pereulok Rogatinsky, 56, kv. 1; Galina M. Tsukanova, prospekt Moskovsky, 198/2, kv. 66; Valentin A. Oridoroga, ulitsa Sotsialisticheskava, 15, all of Kharkov; Alexandr A. Shalimov, ulitsa Kirova, 34"A", kv. 59, Kiev; Jury A. Furmanov, prospekt Nauki, 142, korpus 12, kv. 4, Kiev; Valery P. Silchenko, ulitsa Krasnoarmeiskaya, 101, kv. 20, Kiev; Sergei A. Shalimov, ulitsa Plekhanova, 4"A", kv. 93, Kiev; Yaroslav I. Khadzhai, prospekt Lenina, 48"A", kv. 36, Kharkov; Galina V. Obolentseva, ulitsa Prodolnaya, 3"B", kv. 28, Kharkov; Nikolai E. Vorobiev, ulitsa Prodolnaya, 3"B", kv. 65, Kharkov, all of U.S.S.R.

[21] Appl. No.: 258,832

[22] Filed: Apr. 29, 1981

[51] Int. Cl.³ .............................................. A61L 17/00
[52] U.S. Cl. ............................... 128/335.5; 8/116 R; 8/120; 8/181
[58] Field of Search ............ 128/335.5; 8/120, 116 R, 8/181

[56] References Cited

U.S. PATENT DOCUMENTS

| | | | |
|---|---|---|---|
| 2,537,978 | 1/1951 | Eberl | 128/335.5 |
| 2,537,979 | 1/1951 | Eberl | 128/335.5 |
| 2,764,159 | 9/1956 | Masci et al. | 128/335.5 |
| 3,499,449 | 3/1970 | Smith | 128/335.5 |
| 3,757,786 | 9/1973 | Smith | 128/335.5 |

*Primary Examiner*—Allan Lieberman
*Attorney, Agent, or Firm*—Ladas & Parry

[57] ABSTRACT

An absorbable surgical suture material based on monocarboxycellulose having the general formula

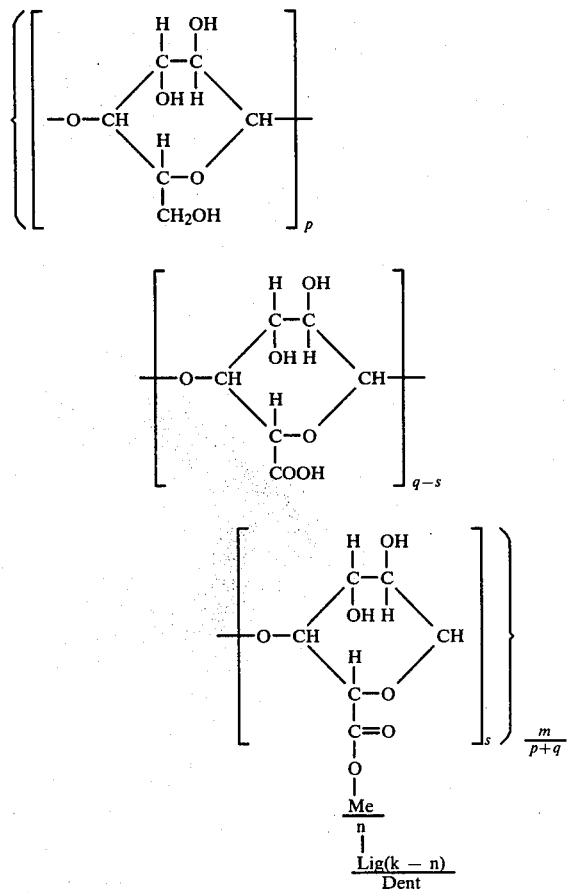

where:
m is a degree of polymerization of the initial cellulose from 250 to 3,300;
p is a molar fraction of D-glucopyranose cycles in one polymer period from 0.95 to 0.05;
q is a molar fraction of cycles of d-anhydroglucuronic acid from 0.05 to 0.95;
S is a molar fraction of the complex fragment of D-anhydroglucuronic acid, metal, and ligand from 0.03 to 0.55;
Me is a transition metal;
n is a valence of the transition metal;
k is a coordination number of the transition metal $\geq 4$;
Lig is polydentate ligands;
Dent is a dentation of the ligands $\geq 2$.

A method for producing said material consists in that cellulose threads are first threaded with nitrogen oxides, then for 0.5 to 2.0 hours treated with a 0.5–2.0-percent solution of a salt of a transition metal with a coordination number not less than 4 in a suitable solvent, and after this treated for 0.5 to 2.0 hours with a 1.0–2.0-percent solution of a polydentate complexing agent in a suitable solvent.

2 Claims, No Drawings

ABSORBABLE SURGICAL SUTURE MATERIAL BASED ON MONOCARBOXYCELLULOSE AND METHOD FOR PRODUCING THE SAME

FIELD OF THE INVENTION

The present invention relates to an absorbable surgical suture material based on monocarboxycellulose and method for producing thereof.

Said material is intended to join tissues by surgical sutures and may find application in medicine, biology, and veterinary practice.

The use of absorbable suture materials in surgical practice has long been known. Such materials obviate the need for an additional procedure of suture removal.

The demands placed upon said materials get over more stringent in the course of time. Modern absorbable surgical suture materials should offer an adequate mechanical strength in both dry and moist states, elasticity, as well as a combination of additional properties, the most important of which are:

a concordance between the time of disintegration and hence also of a drop in the mechanical strength of the absorbable surgical suture material and the wound healing time;

absence of allergic and inflammatory reactions in application of sutures and over the period of a complete absorption of the suture material.

One more property essential in modern suture materials is that their colour should be in contrast with respect to the blood and wound tissues, which is needed to facilitate surgical manipulations.

Absorbable suture materials from animal intestines, i.e., catgut and chromic catgut, which have found an extensive application in the surgical practice feature an allergizing effect and a pronounced inflammatory reaction in biologic tissues resulting in a coarse cicatrization and deformation of the latter, and therefore their use at present is being sharply limited.

The surgical practice has gained a many-year experience of a successful use of oxidized cellulose-based hemostatic materials. Such materials as well as the products of their disintegration, glucose and glucuronic acid, are known to exert no toxic and allergenic effect on the organism. In addition, cellulose is a readily available and cheap raw material.

Attempts to utilize oxidized cellulose for producing an absorbable suture material have also been known, but the produced materials featured a low mechanical strength, which prevented their extensive and dependable application in the surgical practice. That is why further developments of methods for producing oxidized cellulose-based absorbable surgical suture materials offering a higher mechanical strength are being continued.

DESCRIPTION OF THE PRIOR ART

There have been proposed surgical threads (U.S. Pat. No. 2,537,979) produced through cellulose oxidation by nitrogen oxides, the oxidation being carried out till attaining a carboxyl group content of 4 to 12.5%.

The process of producing said surgical threads lasts 64 hours and is conducted at a temperature of 25° C. After treating the threads with nitrogen oxides has been completed, the threads are washed with distilled water and dried. The ratio of the tensile strength of the threads after treating with nitrogen oxides to that of the initial threads is of 36.8–43.5%, i.e. the loss of strength is of 63.2% to 56.5%.

The low tensile strength of the surgical threads produced in accordance with said invention greatly impedes surgical manipulations, since it fails to exclude such postoperative complications as a separation of wound edges.

Furthermore, an absorbable surgical thread produced in accordance with U.S. Pat. No. 2,537,979 completely lost the mechanical strength in 5 days in the tests conducted in a phosphate buffer solution of pH 7.5 at 37° C., where the thread disintegration process proceeds slower than in living tissues. No tests of said thread with living tissues are described in said patent.

SUMMARY OF THE INVENTION

A principal object of the present invention is to provide an absorbable surgical suture material based on monocarboxycellulose, which allows its disintegration time to be matched with the wound healing time and brings about no allergic and inflammatory reactions both in the application of sutures and over the period of a complete absorption of the suture material.

A not less important object of the invention is to provide an absorbable surgical suture material whose colour is in contrast with the background of the blood and biologic tissues.

Another object of the invention is to upgrade the mechanical strength of the suture material.

Still another important object of the present invention is to provide a method for producing an absorbable surgical suture material based on monocarboxycellulose.

Other objects and advantages of the present invention will become apparent from the following description thereof.

The above-mentioned and other objects are attained by that there is proposed an absorbable surgical suture material based on monocarboxycellulose having the general formula:

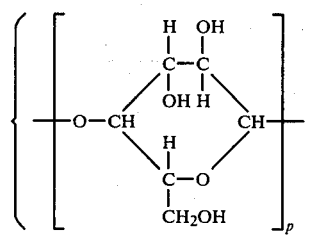

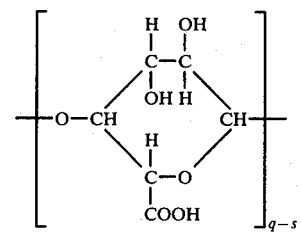

-continued

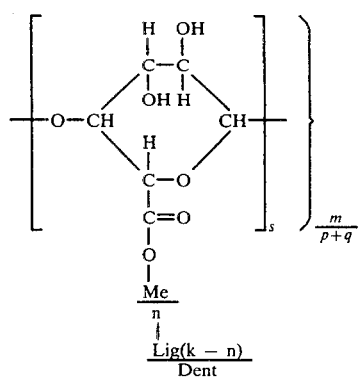

where:

m = degree of polymerization of the initial cellulose from 250 to 3300;

p = molar fraction of d-glucopyranose cycles in one polymer period from 0.95 to 0.05;

q = molar fraction of cycles of d-anhydroglucuronic acid from 0.05 to 0.95;

S = molar fraction of the complex fragment of d-anhydroglucuronic acid, metal, and ligand from 0.03 to 0.55;

Me = transition metal;

n = valence of the transition metal;

k = coordination number of the transition metal $\geq 4$;

Lig = polydentate ligands;

Dent = dentation of the ligands $\geq 2$.

Such suture material based on monocarboxycellulose which also may be called suture material of complex monocarboxycellulose-metalligand compounds in the form of thread has been tested by conducting a series of operations on four species of experimental animals of both sexes: white laboratory rats weighing 150–200 g; guinea pigs weighing 250 g; short-haired rabbits of the chinchilla breed weighing 3–4 kg; and mongrel dogs weighing 12–15 kg.

The test results are listed in Table 1.

TABLE 1

| Item No. | Operation | Number of experiments | Animal species | | | |
|---|---|---|---|---|---|---|
| | | | White rats | Guinea pigs | Rabbits | Dogs |
| 1 | 2 | 3 | 4 | 5 | 6 | 7 |
| 1 | Skin and muscle suturing | 63 | 63 | — | — | — |
| 2 | Liver tissue stitching | 89 | 81 | 8 | — | — |
| 3 | Stomach wall suturing | 180 | 160 | — | 10 | 10 |
| 4 | Enteroplasty | 67 | 10 | — | 47 | 10 |
| 5 | Colonoplasty | 34 | — | — | 24 | 10 |
| 6 | Large-small intestinal anastomosis | 10 | — | — | 10 | — |
| 7 | Cholecystostomyorraphy | 26 | — | — | 24 | 2 |
| 8 | Application of cholecystenteroanastomosis | 15 | — | — | 9 | 6 |
| 9 | Application of pancreatoduodenoanastomosis | 8 | — | — | — | 8 |

The above-specified thread has thus been tested on the principal experimental models simulating the surgical operations conducted under clinical conditions.

In its manipulation properties the proposed suture material offers a strength which allows making the main types of both interrupted and continuous surgical sutures such as single interrupted, blanket, U-shaped, purse-string, Connell's, Shmiden's, Matyshak's, etc. The thread is easily tied into all types of surgeons knots, slides through tissues in both dry and moist states and, owing to its softness and elasticity, does not traumatize the tissues of parenchymatous and hollow organs.

As little as two knots tied in an arbitrary manner sufficed for holding the sutures. Ends of the thread after its cutting neither protruded nor traumatized the tissues. The thread did not get fluffy at bends and in threading it into surgeon's needle eyes. Owing to a high elasticity, such a thread can take the shape of the tissues being joined, not deforming the latter.

In the organism, the thread of complex monocarboxycellulose-metal-ligand compounds disintegrated and got absorbed.

Changes in the suture material during absorption are given in Table 2.

Thus, in the course of disintegration said thread goes through a series of successive transformations accompanied by certain morphological changes in tissues and structural changes in the thread.

At first the thread of complex monocarboxycellulose-metal-ligand compounds loses the strength because of swelling. Said thread disintegrates into fragments which lose the fibrous structure and homogenize, turning into a homogeneous mass. Histologic investigations have shown that a thin membrane made up of connective tissue cells originates around the fibres of such a thread. The thickness of such a membrane is not more than 20 to 30 fibroblast layers and in 1–2 months after the operation diminishes to 5 to 10 such layers, which evidences an insignificant response of the organism to the implantation of the proposed suture material.

TABLE 2

| Absorption stage | Absorption form | Morphological features |
|---|---|---|
| 1 | 2 | 3 |
| I. Early changes | (1) Structure retention | Absence of absorption symptoms |
| | (2) Swelling | Imbibition by albuminous liquid |
| II. Late changes | (3) Loss of strength | Thread retains fibrous structure, but offers no mechanical strength |
| | (4) Fragmentation | Thread seperates into segments (weakening of interfibrous bonds) |
| | (5) Homogenization | Transformation into amorphous substance |
| | (6) Full resorption | Absorption by macrophages |
| | (7) Trace reactions | Cicatrization of suture channels |

The thread is subsequently absorbed by giant cells and macrophages, accumulates as a homogenous gray mass in their cytoplasm, and these cells in 6 to 12 months discharge it out of the organism via capillaries and lymphatic vessels. A skin cicatrix and fatty tissue develop in the place of such thread, which should be regarded as a favourable reaction of the organism.

In Table 3 there is given, by way of example, the time of mechanical strength loss and of complete absorption of the claimed suture material.

TABLE 3

| Nos. | Nominal diameter, mm | Loss of strength, days | Complete absorption, months |
|---|---|---|---|
| 1 | 0.40–0.45 | 10 | 6 |
| 2 | 0.50–0.55 | 14 | 8–12 |
| 3 | 0.80–0.85 | 15–20 | 12 |

The thread of complex monocarboxycellulose-metal-ligand compounds was used for the application of interorgan anastomoses with stitching mucous membranes, muscular layers and all layers of the organs being sutured by both interrupted and continuous sutures. In most of operations on esophagous, stomach, and duodenum said thread was used in place of catgut for application of the first row of sutures; in application of interintestinal anastomoses of the Brown's type, said thread alone was used as the suture material.

The proposed suture material was also used for carrying out appendectomy, in mastectomies, for lung aerostases, stitching the gallbladder bed, stitching a wound on the liver, for sutures on the subcutaneous fat cellulose, for suturing skin wounds and in other cases. Postoperational sutures were characterized with good cosmetic appearance.

Endoscopy in the postoperative period showed that inflammatory changes in the gastroenteric tract of patients corresponded to the severity of the accomplished intervention and stopped in 2 to 3 weeks. In 2 to 3 months after the operation the endoscopic picture corresponded to the changes observed in 1 year with the use of catgut for similar purposes.

No postoperative complications which could be attributed to the use of the proposed suture material were observed.

CLINICAL EXAMPLES

1. Patient A. Operation on Aug. 7, 1979: colonic substernal esophagoplasty.

The anastomosis between large intestine lengths of the "end-to-end" type, between the stomach and the large-intestinal transplant of the "end-to-side" type, and between the esophagus and the transplant of the "end-to-end" type was made with the use of the thread of complex monocarboxycellulose-metal-ligand compound (mucous-submucous sutures).

The patient was discharged from hospital in a satisfactory state with no complications. The functions of all the anastomoses were good.

2. Patient B. Operation on Aug. 23, 1979: a combined gastrectomy with resection of pancreas body and cauda pancreatis.

Gastroenterostomy was carried out (mucous-submucous sutures were made with the use of said thread). An anastomosis between small intestine loops (the Brown's anastomosis) has been fully performed with the thread of complex monocarboxycellulose-metal-ligand compounds (two rows of sutures).

The patient was discharged with no complications.

3. Patient C. Operation on Jan. 30, 1980: intrathoracic gastroplasty, intussusceptional esophagogastrostomy. The anastomosis was performed (mucous-submucous suture) with said thread.

The postoperative period was without complications.

In 30 days after the operation the thread was not detected by endoscopy. The anastomosis was with no inflammatory changes and its appearance corresponded to that observed in 8–12 months after operation with the use of catgut.

These and other objects are attained also by that in a method for producing an absorbable surgical suture material based on monocarboxycellulose by treating cellulose threads with nitrogen oxides, according to the invention, after the treatment with nitrogen oxides the cellulose threads are additionally treated for 0.5 to 2.0 hours with 0.5–2.0 percent solution of a salt of a transition metal having a coordination number of not less than 4 in water or in a suitable organic solvent and then for 0.5 to 2.0 hours with a 1.0–2.0 percent solution of a polydentate complexing agent in water or in a suitable organic solvent.

Investigations conducted on both artificial media and living organisms have established that surgical threads made from the proposed material offer a higher mechanical strength. This stems from the formation of additional cross-links between the molecules of monocarboxycellulose. Such cross-links originate owing to the polyvalency and high coordination number of transition metals as well as to the polydentate character of ligands. This fact along with a relatively high strength of the bond in the forming complex compounds promote slowing down the process of absorption of the surgical threads in a living organism (disintegration), which allows the time, whereover the mechanical strength of tissues drops (the threads get absorbed), to be matched with the time of growth in the cicatrix strength in the course of wound cicatrization.

The rate of absorption may be controlled by adjusting the degree of oxidation of the initial monocarboxycellulose, absorption being more rapid when the degree of oxidation is higher.

For a better understanding of the exact nature of the present invention, the structure of the complex fragment of the general formula may be represented by the following examples:

for a complex compound formed with Cr as the transition metal and ethylene diamine tetraacetic acid as the polydentate complexing agent:

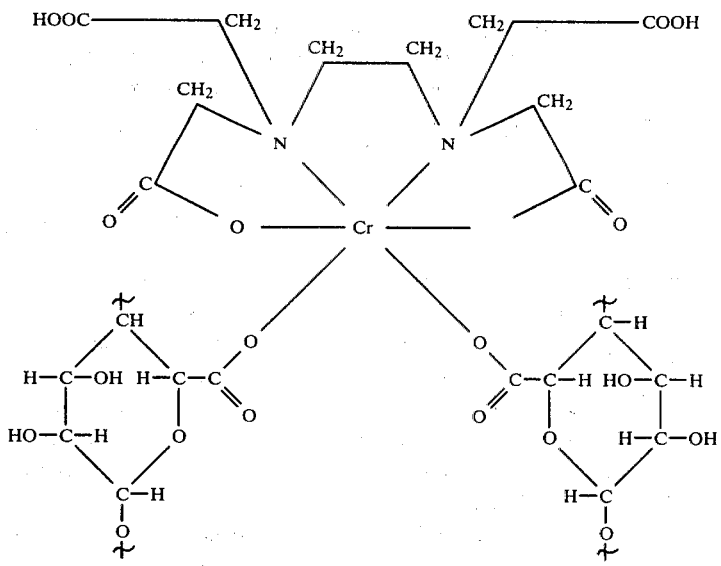

for a complex compound formed with Fe and 8-oxyquinoline:

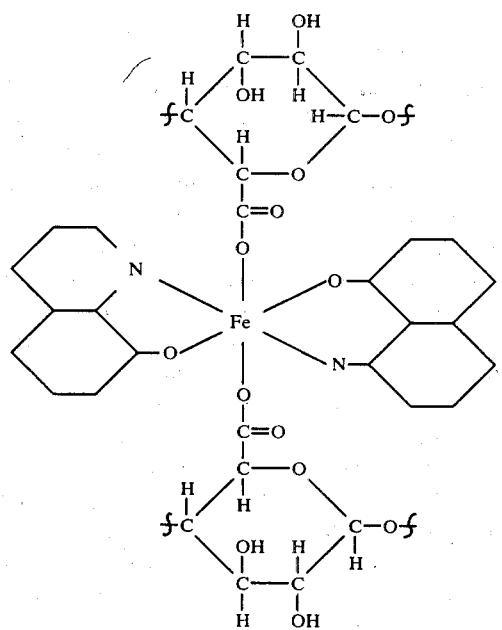

It should be pointed out that surgical threads of the proposed material are harmless and bring about no allergic and inflammatory reactions in the application of sutures and over the period of the complete absorption of the thread.

This is due to the fact that the products of disintegration of monocarboxycellulose-metal-ligand complexes are neither toxic for living organisms nor feature antigenic properties.

Furthermore, the colour of said threads is in contrast with the background of the blood and biologic tissues, it is persistent, not washed out by biologic media, remaining till the end of thread absorption, which greatly facilitates the application of sutures on a wound and allows observing the entire absorption period. This advantage stems from that the colour of the threads is inherent in the thread substance itself rather than due to additions of pigments. Owing to this, surgical threads made from the proposed material, used to join tissues by surgical sutures, are completely absorbed as the wound heals and leave no tattooing traces on tissues. The above-specified procedures and conditions of the method of the invention provide for attaining the above-described effect.

To produce a surgical suture material, a thread from which exerts no general and local effects on a living organism in the course of the application of a suture and over the period of absorption of the thread, it is expedient to employ as the solution of a transition metal salt solutions of salts of Fe, Ni, Cr, Bi, or Mn or their mixtures in water or in a suitable organic solvent; it is appropriate to use as the polydentate complexing agent a solution of tannin, gallic acid, ethylene diamine tetraacetic acid, 8-oxyquinoline, or quinosol in water or in a suitable organic solvent.

One more aspect of the invention consists in that there is proposed an absorbable surgical suture material wherein complex monocarboxycellulose-metal-ligand compounds have a degree of polymerization of the initial cellulose of 250 to 3,300; a molar fraction of D-glucopyranose cycles in one polymer period of 0.88 to 0.60; a molar fraction of cycles of D-anhydroglucuronic acid of 0.12 to 0.40; and a molar fraction of a complex fragment of D-anhydroglucuronic acid, metal, and ligands of 0.04 to 0.24.

Such a material features hemostatic properties and a higher mechanical strength.

Hemostatic properties of the proposed suture material are explained by the presence of a certain number of free carboxyls not bonded into complex compounds.

To produce said material there is proposed a method consisting in that cellulose threads are treated with nitrogen oxides and after this are treated for 0.5 to 2.0 hours first with 0.5–2.0 percent solution of Fe, Ni, Cr, Bi, or Mn salt in water or in a suitable organic solvent till an ion exchange degree of 25 to 60% is attained and then with 1.0–2.0 percent solution of tannin, gallic acid, ethylene diamine tetraacetic acid, 8-oxyquinoline, or quinosol in water or in a suitable organic solvent.

DESCRIPTION OF THE PREFERRED EMBODIMENTS

In accordance with the method of the invention, an absorbable surgical suture material of complex monocarboxycellulose-metal-ligand compounds is produced as follows.

Cellulose threads are subjected to oxidation with nitrogen oxides till monocarboxycellulose is obtained. Employed as the cellulose threads are cotton, flaxen, viscose, Polynosic ones, etc. which have a broad range of the thickness of fibres and of the number of ends. The oxidation is carried out by conventional methods. It is most effective to conduct oxidation of cellulose threads with nitrogen oxides in an organic solvent at a temperature of −11° to +21° C. with subsequently extracting the cellulose threads from the organic solvent and maintaining them at a temperature of 30° to 70° C. and a pressure of 506 to 1519 hPa. The oxidized threads are thoroughly washed with water.

The wet threads are placed into a stainless-steel reaction vessel of 20 l in capacity, filled with a 0.5–2.0 percent solution of a transition metal salt in water or in a suitable organic solvent, for 0.5 to 2.0 hours.

Next, the threads are extracted from the working solution and once again washed with water.

Used as the solution of a transition metal salt may be solutions of Fe, Ni, Cr, Bi, or Mn salts or mixtures thereof in water or in a suitable organic solvent.

The washed threads are immersed into a reaction vessel of 20 l in capacity, filled with a 1.0–2.0 percent solution of a polydentate complexing agent in water or in a suitable organic solvent, for 0.5 to 2.0 hours.

Used as the above-mentioned solution is a solution of tannin, gallic acid, ethylene diamine tetraacetic acid, 8-oxyquinoline, or quinosine in water or in a suitable organic solvent. The threads thus obtained are then tested for the content of the transition metal, relative moisture content, and tensile strength.

The proposed suture material may be also used for making napples, bandages, cotton wool, tampons and other non-woven articles used in surgical practice.

EXAMPLE 1

An absorbable surgical suture material in accordance with the proposed procedure was produced as follows.

1.2 kg of viscose threads No. 60/12 having a tensile strength of 2.20 kg were oxidized with nitrogen oxides by one of known methods till obtaining monocarboxycellulose with a carboxyl group content of 9.8%.

The wet threads were placed for 1 hour into a reaction vessel of 20 l in capacity, filled with 16 l of 1.0 percent aqueous solution of $Cr(NO_3)_3$. After this the treads were extracted from the solution and washed with water.

Next, the washed threads were immersed for 1 hour into a reaction vessel of 20 l in capacity, filled with 16 l of 1.0 percent solution of 8-oxyquinoline in ethanole.

The threads thus processed were of orange colour. They were washed with water and dried in an air stream.

The obtained threads were tested for the content of the transition metal, relative moisture content, and tensile strength.

The test results were as follows:

| | |
|---|---|
| content of transition metal, % | 1.99 |
| relative moisture content, % | 12.5 |
| tensile strength, kg | 2.45 |
| ratio of tensile strength of processed threads to that of initial threads, % | 111 |

EXAMPLE 2

An absorbable surgical suture material was produced in accordance with the proposed procedure.

Viscose threads with the same initial characteristics as in Example 1 were processed according to the procedure described in Example 1.

Said threads were treated first with a 1 percent aqueous solution of $Cr(CH_3COO)_3$ for 1.5 hours and then with a 2 percent solution of gallic acid in ethanol for 1 hour.

The threads thus processed were of green colour.

The obtained threads were tested as described in Example 1.

The test results were as follows:

| | |
|---|---|
| content of transition metal, % | 2.13 |
| relative moisture content, % | 12.6 |
| tensile strength, kg | 2.40 |
| ratio of tensile strength of processed threads to that of initial threads, % | 109 |

EXAMPLE 3

An absorbable surgical suture material was produced in accordance with the proposed procedure.

0.4 kg of strengthened viscose threads No. 20/2 having a tensile strength of 2.10 kg were oxidized with nitrogen oxides by one of known methods till obtaining monocarboxycellulose with a carboxyl group content of 3.5%, and then were processed in accordance with the procedure described in Example 1.

Said threads were treated first with a 2 percent aqueous solution of $Cr(NO_3)_3$ for 2 hours and then with a 2 percent solution of 8-oxyquinoline in ethanol for 2 hours.

The threads thus processed were of orange colour.

The obtained threads were tested as described in Example 1.

The test results were as follows:

| | |
|---|---|
| content of transition metal, % | 0.38 |
| relative moisture content, % | 7.8 |
| tensile strength, kg | 3.0 |
| ratio of tensile strength of processed threads to that of initial threads, % | 142 |

EXAMPLE 4

An absorbable surgical suture material was produced in accordance with the proposed procedure.

Strengthened viscose threads with the same initial characteristics as in Example 3 were processed in accordance with the procedure described in Example 1.

Said threads were treated first with a 1.5 percent aqueous solution of $Cr(NO_3)_3$ for 1 hour and then with a 1.5 percent solution of tannin in ethanol for 1 hour.

The threads thus processed were of green colour.

The obtained threads were tested as described in Example 1.

The test results were as follows:

| | |
|---|---|
| content of transition metal, % | 0.30 |
| relative moisture content, % | 7.95 |
| tensile strength, kg | 2.45 |
| ratio of tensile strength of processed threads to that of initial threads, % | 116 |

EXAMPLE 5

An absorbable surgical suture material was produced in accordance with the proposed procedure.

Strengthened viscose threads with the same initial characteristics as in Example 3 were processed in accordance with the procedure described in Example 1.

Said threads were treated first with a 1.5 percent aqueous solution of $Cr(NO_3)_3$ for 1 hour and then with a 1.5 percent aqueous solution of ethylene diamine tetraacetic acid for 1 hour.

The threads thus processed were of white colour.

The obtained threads were tested as described in Example 1.

The test results were as follows:

| | |
|---|---|
| content of transition metal, % | 0.305 |
| relative moisture content, % | 7.7 |
| tensile strength, kg | 2.50 |
| ratio of tensile strength of processed threads to that of initial threads, % | 119 |

EXAMPLE 6

An absorbable surgical suture material was produced in accordance with the proposed procedure.

0.4 kg of Polynosic threads No. 60/3 having a mechanical tensile strength of 0.85 kg were oxidized with nitrogen oxides by one of known methods till obtaining monocarboxycellulose with a carboxyl group content of 3.5% and then were processed in accordance with the procedure described in Example 1.

Said threads were treated first with a 1.5 percent aqueous solution of $NiCl_2$ for 1 hour and then with a 2 percent solution of gallic acid in 70 percent ethanol for 1 hour.

The threads thus processed were of green colour.

The obtained threads were tested as described in Example 1.

The test results were as follows:

| | |
|---|---|
| content of transition metal, % | 0.59 |
| relative moisture content, % | 7.85 |
| tensile strength, kg | 1.0 |
| ratio of tensile strength of processed threads to that of initial threads, % | 117 |

EXAMPLE 7

An absorbable surgical suture material was produced in accordance with the proposed procedure.

Polynosic threads with the same initial characteristics as in Example 6 were processed in accordance with the procedure described in Example 1.

Said threads were treated first with a 2 percent aqueous solution of $NiCl_2$ for 1 hour and then with a 2 percent solution of 8-oxyquinoline in 10 percent ethanol for 1 hour.

The threads thus processed were of green colour.

The obtained threads were tested as described in Example 1.

The test results were as follows:

| | |
|---|---|
| content of transition metal, % | 0.62 |
| relative moisture content, % | 7.9 |
| tensile strength, kg | 1.05 |
| ratio of tensile strength of processed threads to that of initial threads, % | 124 |

EXAMPLE 8

An absorbable surgical suture material was produced in accordance with the proposed procedure.

1.2 kg of viscose threads No. 60/12 having a tensile strength of 2.57 kg were oxidized with nitrogen oxides by one of known methods till obtaining monocarboxycellulose with a carboxyl group content of 5.9% and then were processed in accordance with the procedure described in Example 1.

Said threads were treated first with a 1 percent aqueous solution of $NiCl_2$ for 1 hour and then with a 2 percent aqueous solution of quinosol for 1 hour.

The threads thus processed were of bright green colour.

The obtained threads were tested as described in Example 1.

The test results were as follows:

| | |
|---|---|
| content of transition metal, % | 1.37 |
| relative moisture content, % | 8.4 |
| tensile strength, kg | 2.85 |
| ratio of tensile strength of processed threads to that of initial threads, % | 111 |

EXAMPLE 9

An absorbable surgical suture material was produced in accordance with the proposed procedure.

Viscose threads with the same initial characteristics as in Example 8 were processed in accordance with the procedure described in Example 1.

Said threads were treated first with a 2 percent aqueous solution of $NiCl_2$ for 1 hour and then with a 2 percent solution of 8-oxyquinoline in dimethyl sulphoxide for 1 hour.

The threads thus processed were of bright green colour.

The obtained threads were tested as described in Example 1.

The test results were as follows:

| | |
|---|---|
| content of transition metal, % | 1.51 |
| relative moisture content, % | 8.2 |
| tensile strength, kg | 3.10 |
| ratio of tensile strength of processed threads to that of initial threads, % | 121. |

EXAMPLE 10

An absorbable surgical suture material was produced in accordance with the proposed procedure.

0.4 kg of strengthened viscose threads No. 60/4 having a tensile strength of 1.33 kg were oxidized with nitrogen oxides by one of known methods till obtaining monocarboxycellulose with a carboxyl group content of 6.8% and then were processed in accordance with the procedure described in Example 1.

Said threads were treated first with a 2 percent aqueous solution of $NiCl_2$ for 1 hour and then with a 2 percent solution of 8-oxyquinoline in dimethyl formamide for 1 hour.

The threads thus processed were of bright green colour.

The obtained threads were tested as described in Example 1.

The test results were as follows:

| | |
|---|---|
| content of transition metal, % | 1.94 |
| relative moisture content, % | 8.6 |
| tensile strength, kg | 1.62 |
| ratio of tensile strength of processed threads to that of initial threads, % | 122 |

EXAMPLE 11

An absorbable surgical suture material was produced in accordance with the proposed procedure.

Strengthened viscose threads with the same initial characteristics as in Example 10 were processed in accordance with the procedure described in Example 1.

Said threads were treated first with a 1.5 percent aqueous solution of $NiSO_4$ for 1 hour and then with a 2 percent solution of tannin in ethanol for 1 hour.

The threads thus processed were of dark-green colour.

The obtained threads were tested as described in Example 1.

The test results were as follows:

| | |
|---|---|
| content of transition metal, % | 1.80 |
| relative moisture content, % | 8.8 |
| tensile strength, kg | 1.53 |
| ratio of tensile strength of processed threads to that of initial threads, % | 115 |

EXAMPLE 12

An absorbable surgical suture material was produced in accordance with the proposed procedure.

0.6 kg of cotton threads No. 100/18 having a tensile strength of 2.31 kg were oxidized with nitrogen oxides by one of known method till obtaining monocarboxycellulose with a carboxyl group content of 6.3% and then were processed in accordance with the procedure described in Example 1.

Said threads were treated first with a 1 percent aqueous solution of $BiBr_3$ for 2 hours and then with a 1 percent solution of 8-oxyquinoline in 10 percent ethanol for 2 hours.

The threads thus processed were of green colour.

The obtained threads were tested as described in Example 1.

The test results were as follows:

| | |
|---|---|
| content of transition metal, % | 3.12 |
| relative moisture content, % | 8.45 |
| tensile strength, kg | 2.62 |
| ratio of tensile strength of processed threads to that of initial threads, % | 110 |

EXAMPLE 13

An absorbable surgical suture material was produced in accordance with the proposed procedure.

0.4 kg of Polynosic threads having a tensile strength of 0.62 kg were oxidized with nitrogen oxides by one of known methods till obtaining monocarboxycellulose with a carboxyl group content of 5.0% and then were processed in accordance with the procedure described in Example 1.

Said threads were treated first with a 2 percent solution of $Bi(NO_3)_3$ in 10 percent aqueous solution of $CH_3COOH$ for 2 hours and then with a 2 percent solution of tannin in ethanol for 2 hours.

The threads thus processed were of yellow colour.

The obtained threads were tested as described in Example 1.

The test results were as follows:

| | |
|---|---|
| content of transition metal, % | 2.56 |
| relative moisture content, % | 8.1 |
| tensile strength, kg | 0.80 |
| ratio of tensile strength of processed threads to that of initial threads, % | 129 |

EXAMPLE 14

An absorbable surgical suture material was produced in accordance with the proposed procedure.

1.2 kg of viscose threads No. 60/12 having a tensile strength of 2.03 kg were oxidized with nitrogen oxides by one of known methods till obtaining monocarboxycellulose with a carboxyl group content of 10.0% and then were processed in accordance with the procedure described in Example 1.

Said threads were treated first with a 2 percent aqueous solution of $FeCl_3$ for 1 hour and then with a 2 percent solution of quinosol in 10 percent ethanol for 2 hours.

The threads thus processed were of black colour.

The obtained threads were tested as described in Example 1.

The test results were as follows:

| | |
|---|---|
| content of transition metal, % | 1.15 |
| relative moisture content, % | 12.8 |
| tensile strength, kg | 2.74 |
| ratio of tensile strength of processed threads to that of initial threads, % | 135 |

EXAMPLE 15

An absorbable surgical suture material was produced in accordance with the proposed procedure.

0.4 kg of strengthened viscose threads No. 20/2 having a tensile strength of 2.1 kg were oxidized with nitrogen oxides by one of known methods till obtaining monocarboxycellulose with a carboxyl group content of 3.6% and then were processed in accordance with the procedure described in Example 1.

Said threads were treated first with a 2 percent solution of $FeCl_3$ in dimethyl sulphoxide for 2 hours and then with a 2 percent aqueous solution of quinosol for 2 hours.

The threads thus processed were of grey colour.

The obtained threads were tested as described in Example 1.

The test results were as follows:

| | |
|---|---|
| content of transition metal, % | 0.41 |
| relative moisture content, % | 7.6 |
| tensile strength, kg | 3.12 |
| ratio of tensile strength of processed threads to that of initial threads, % | 148. |

EXAMPLE 16

An absorbable surgical suture material was produced in accordance with the proposed procedure.

0.6 kg of cotton threads No. 100/18 having a tensile strength of 2.32 kg were oxidized with nitrogen oxides by one of known methods till obtaining monocarboxycellulose with a carboxyl group content of 7.9% and then processed in accordance with the procedure described in Example 1.

Said threads were treated first with a 1.5 percent aqueous solution of $FeCl_3$ for 1 hour and then with a 1.5 percent solution of tannin in dimethyl sulphoxide for 1 hour.

The threads thus processed were of black colour.

The obtained threads were tested as described in Example 1.

The test results were as follows:

| | |
|---|---|
| content of transition metal, % | 0.86 |
| relative moisture content, % | 9.8 |
| tensile strength, kg | 3.0 |
| ratio of tensile strength of processed threads to that of initial threads, % | 129 |

EXAMPLE 17

An absorbable surgical suture material was produced in accordance with the proposed procedure.

0.4 kg of strengthened viscose threads No. 60/3 having a tensile strength of 0.95 kg were oxidized with nitrogen oxides by one of known methods till obtaining monocarboxycellulose with a carboxyl group content of 4.3% and then processed in accordance with the procedure described in Example 1.

Said threads were treated first with a 2 percent aqueous solution of $MnSO_4$ for 1 hour and then with a 2 percent solution of 8-oxyquinoline in 70 percent ethanol for 1 hour.

The threads thus processed were of green colour.

The obtained threads were tested as described in Example 1.

The test results were as follows:

| | |
|---|---|
| content of transition metal, % | 0.61 |
| relative moisture content, % | 7.0 |
| tensile strength, kg | 1.20 |
| ratio of tensile strength of processed threads to that of initial threads, % | 126 |

EXAMPLE 18

An absorbable surgical suture material was produced in accordance with the proposed method as follows.

0.6 kg of flax threads No. 22/3 having a tensile strength of 0.95 kgf were oxidized with nitrogen oxides by one of known methods till obtaining monocarboxycellulose with a carboxyl content of 5,6%.

The wet threads were placed for 1 hour into a reaction vessel of 20 l in capacity, filled with 16 l of 0.5 percent aqueous solution of $MnSO_4$. After this the threads were extracted from the solution and washed with water. Next, the washed threads were immersed for 1 hour into a reaction vessel of 20 l in capacity, filled with 16 l of 2.0% solution of tannin in ethanol.

The threads thus processed were of green colour. They were washed in water and dried in a flow of air.

The obtained threads were tested for the content of the transition metal, relative moisture and tensile strength.

The tests results were as follows:

| | |
|---|---|
| Content of transition metal, % | 1.18 |
| Relative moisture content, % | 8.3 |
| Tensile strength, kg | 1.42 |
| Ratio of tensile strength of processed threads to that of initial threads, % | 100 |

EXAMPLE 19

An absorbable surgical suture material was produced in accordance with the proposed method.

0.4 kg of viscose strengthened threads No. 60/4 having a tensile strength of 1.33 kg were oxidized with nitrogen oxides by one of known methods till obtaining monocarboxycellulose with a carboxyl content of 6.8% and then were treated as follows.

The threads were first treated with a 1% aqueous solution of $NiCl_2$ for 1 hour, then with a 2% aqueous solution of $FeCl_3$ for 2 hours and after this with a 2% aqueous solution of tannin for 1.5 hour.

The threads thus processed were of dark grey colour.

The tests results were as follows:

| | |
|---|---|
| Content of transition metal, % | 0.95 Fe |
| | 1.23 Ni |
| Relative moisture content, % | 8.9 |
| Tensile strength, kg | 1.42 |
| Ratio of tensile strength of processed threads to that of initial threads, % | 106 |

EXAMPLE 20 an absorbable surgical suture material was produced in accordance with the proposed method.

0.6 kg of Polynosic threads No. 51/15 having a tensile strength of 3.6 kg were oxidized with nitrogen oxides by one of known methods till obtaining monocarboxycellulose with a carboxyl content of 4.25% and then were treated as follows.

The threads were first treated with a 0.5% aqueous solution of $Cr(CH_3COO)_3$ for 1 hour, after which with a 1% aqueous solution of $FeCl_3$ for 1.5 hour and then with a 1.5% aqueous solution of gallic acid for 2 hours.

The threads thus processed were of dark grey colour.

The obtained threads were tested as described in Example 1.

The test results were as follows:

| | |
|---|---|
| Content of transition metal, % | 0.30 Cr |
| | 0.46 Fe |
| Relative moisture content, % | 7.8 |
| Tensile strength, kg | 3.65 |
| Ratio of tensile strength of processed threads to that of initial threads, % | 101 |

While particular embodiments of the invention have been shown and described, various modifications thereof will be apparent to those skilled in the art and therefore it is not intended that the invention be limited to the disclosed embodiments or to the details thereof and the departures may be made therefrom within the spirit and scope of the invention as defined in the claims.

What is claimed is:

1. An absorbable suture material based on monocarboxycellulose having the general formula:

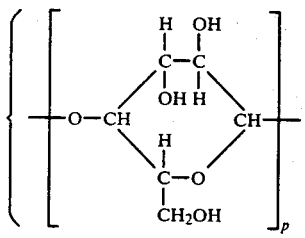

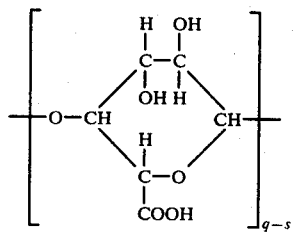

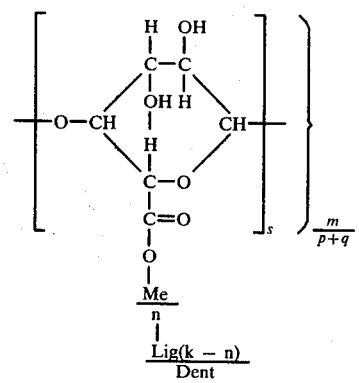

where m is a degree of polymerization of the initial cellulose from 250 to 3.300;

p is a molar fraction of D-glucopyranose cycles in one polymer period from 0.88 to 0.60;

q is a molar fraction of cycles of D-anhydroglucuronic acid from 0.12 to 0.40;

s is a molar fraction of the complex fragment of D-anhydroglucuronic acid, metal and ligand, from 0.04 to 0.24;

Me is a transition metal selected from the group consisting of Fe, Ni, Co, Bi, Mn and a combination thereof;

n is a valency of the transition metal;

K is a coordination number of the transition metal

Lig is polydentate ligands selected from the group consisting of tannin, gallic acid, ethylene diamine tetraacetic acid, 8-oxyquinoline and quinosol; and Dent is a dentation of the ligands.

2. A method for producing an absorbable surgical suture material as claimed in claim 1 comprising:
   (a) treating cellulose threads with nitrogen oxides to obtain monocarboxycellulose threads;
   (b) additionally treating the monocarboxycellulose threads with a 0.5 to 2.0 percent solution of a salt of a transition metal selected from the group consisting of salts of Fe, Ni, Cr, Bi, Mn and mixtures thereof is a suitable solvent for 0.5 to 2.0 hours to obtain a monocarboxycellulose salt of a transition metal with an ion exchange degree of 25 to 60%;
   (c) further treating the monocarboxycellulose salt of the transition metal with a 1.0 to 2.0 percent solution of a polydentate complexing agent selected from the group consisting of tannin, gallic acid, ethylene diamine tetraacetic acid, 8-oxyquinoline and quinosol in a suitable solvent for 0.5 l to 2.0 hours.

* * * * *